United States Patent [19]

Mitamura et al.

[11] Patent Number: 5,618,425
[45] Date of Patent: Apr. 8, 1997

[54] FILTERING APPARATUS WITH A PLEATED FILTERING ELEMENT EMBEDDED IN A FILLING MATERIAL

[75] Inventors: Makoto Mitamura; Hidetaka Nakayama, both of Shizuoka-ken, Japan

[73] Assignee: Terumo Kabushiki Kaisha, Tokyo, Japan

[21] Appl. No.: 663,595

[22] Filed: Jun. 14, 1996

Related U.S. Application Data

[63] Continuation of Ser. No. 235,533, Apr. 29, 1994, abandoned.

[30] Foreign Application Priority Data

Apr. 30, 1993 [JP] Japan ................................. 5-128300
Feb. 3, 1994 [JP] Japan ................................. 6-011743

[51] Int. Cl.$^6$ .......................... B01D 19/00; B01D 35/00
[52] U.S. Cl. .................. 210/493.5; 210/435; 210/436; 210/446; 210/472; 210/493.1; 210/496; 210/497.01; 210/497.3; 210/512.1
[58] Field of Search ................................. 210/435, 436, 210/446, 456, 472, 493.1, 493.5, 496, 497.01, 497.3, 512.1

[56] References Cited

U.S. PATENT DOCUMENTS

| | | | |
|---|---|---|---|
| 4,038,194 | 7/1977 | Luceyk et al. | 210/497.3 |
| 4,690,762 | 9/1987 | Katsura | 210/436 |
| 4,919,802 | 4/1990 | Katsura | 210/436 |
| 4,932,987 | 6/1990 | Molina | 210/436 |

FOREIGN PATENT DOCUMENTS

| | | |
|---|---|---|
| 1-148265 | 6/1989 | Japan . |
| 1-148266 | 6/1989 | Japan . |

*Primary Examiner*—John Kim
*Attorney, Agent, or Firm*—Burns, Doane, Swecker & Mathis, LLP

[57] ABSTRACT

A filtering apparatus comprises a housing having a blood inlet and a blood outlet as well as a vent which are formed protrudingly from the housing. A filtering element is provided inside the housing to partition the inside of the housing into a first space and a second space. The filtering element is made from a porous material folded to have a plurality of pleats, the pleated material being arranged to form a hollow truncated cone with the pleats radiating outward. The opening at the top portion of the filtering element is sealed with a filling material. The filling material has a bottom surface that includes a central portion which protrudes into the second space, and this allows a pleat intersecting portion at the outer circumference of the bottom surface to have an inclined surface with respect to the horizontal. Preferably, the outermost diameter of the filtering element gradually increases in the direction from the top portion of the filtering element to the bottom portion thereof, so as to form the shape of a hollow truncated cone. More preferably, a vertical cross section of this conical shaped filtering element reveals a trapezoid with the top and bottom portions thereof forming flat horizontal surfaces.

10 Claims, 6 Drawing Sheets

FILTERING APPARATUS WITH A PLEATED FILTERING ELEMENT EMBEDDED IN A FILLING MATERIAL

This application is a continuation, of application Ser. No. 08/235,533, filed Apr. 29, 1994, now abandoned.

BACKGROUND OF THE INVENTION

1. Field of the Invention

This invention relates to a filtering apparatus, and in particular to a blood filtering apparatus for separating and removing air bubbles and foreign substances from the blood being filtered.

2. Description of the Prior Art

In blood treatment systems in which blood removed from a patient is treated and then returned back to the patient, a filtering apparatus (blood filter) has been employed in the blood flow return line for separating and removing air bubbles and foreign substances from the blood.

These filtering apparatuses are generally referred to as blood filters or bubble traps. In this type of blood filter, a filtering material formed into a pleated shape has been employed to obtain a large filtering surface area, as is mentioned for example in Laid-Open Patent Publications Nos. 1-148265 and 1-148266.

In these prior art blood filters, as is stated for example in Laid-Open Patent Publication No. 1-148265, there is a housing, and in the blood filtering portion of the lower section of the housing, there is provided a filtering material made from a porous material that has been folded to form a plurality of pleats. This filtering material is rolled up within the housing so as to have a cylindrical shape with the pleats radiating outwardly therefrom. Then the open top end of the filtering material is sealed by forming a non-permeable portion obtained from the hardening of a potting material poured across such opening, and this is done in such a way that the interior surface of the non-permeable portion that faces towards the inside of the filtering material is formed as a flat, horizontal surface. Further, the blood outlet that is formed in the lower section of the housing communicates with the interior space of the filtering material.

When these blood filters are primed, the priming fluid enters from the blood outlet and fills up the interior space of the filtering material. At this time, by utilizing the pressure difference between the interior and exterior of the filtering material, any air bubbles existing in the priming fluid are discharged to the outside.

SUMMARY OF THE INVENTION

The object of the present invention is to provide a filtering apparatus with improved bubble separation and removal capabilities.

To achieve the above-mentioned object, a filtering apparatus according to the present invention comprises a housing formed with an inlet and an outlet for a fluid to be treated, and a vent for discharging gas. Positioned inside the housing is a filtering element that partitions the inside of the housing into a first space that communicates with the inlet and a second space that communicates with the outlet, the opening at the top portion of the filtering element being sealed by a filling material. The filtering element is constructed from a porous material sheet that has been folded to form a plurality of pleats, the pleated porous material sheet then being curled together to form a cylindrical shape with the pleats thereof radiating outwards. A central portion of the bottom surface of the filling material has an inclining surface that protrudes into the second space of the housing.

A priming fluid such as saline solution is supplied to the inside of the housing through a tube connected to the outlet. Intermixed with the fluid are tiny bubbles that float up inside the second space until they reach the bottom surface of the filling material. At this time, since the central portion of the bottom surface protrudes into the inside of the second space, with the surface inclining toward the outer circumference thereof, the bubbles are forced by buoyancy to float up along this surface until they enter the inside of the peaks of the pleats, where they pass through the pores of the filtering element, due to the pressure difference between the first space and the second space, to enter into the first space. The bubbles that pass into the first space then float upwardly and are discharged to the outside of the housing through the vent. According to the filtering apparatus of the present invention, as no bubbles remain in the vicinity of the bottom surface of the filling material, there is a substantial improvement with regards to bubble separation. Moreover, in obtaining this improvement, it is not necessary for the volume of the housing to be greater than that used in the prior art, nor are any changes in shape are required. Accordingly, an increase in the amount of the priming fluid is not needed.

Further, during blood treatment, any bubbles that do not readily float up to the top portion of the covering will enter the troughs between the pleats (i.e., the gaps between adjacent pleats). At the innermost portion of the these troughs, the bubbles float up until they reach the bottom surface of the first filling material at the pleat intersecting portion thereof. However, as was previously explained above, since the bottom surface is inclined, the bubbles float up along this inclined surface and exit the troughs. Accordingly, it is possible to prevent bubbles from remaining inside the troughs of the pleats.

Preferably, the filtering element is constructed with the outermost diameter gradually increasing in the direction from the top portion to the bottom portion thereof. Namely, the filtering element is constructed so as to have a hollow truncated conical shape. By forming the filtering element into this shape, a satisfactorily smooth flow of both the blood flowing into the first space and the blood forming a swirly flow within the first space is achieved without having to enlarge the capacity of the housing, or more specifically stated, without having to increase the quantity of priming fluid. As a result, the rate of separation and removal of air bubbles and foreign substances is increased, and in addition to that, it becomes possible to reduce any losses in pressure and to suppress the occurrence of hemolysis. This type of hollow truncated cone-shaped filtering element is obtained, for example, by stretching the bottom portion of the filtering element outwardly after the filling material has been supplied to seal the opening at the top portion thereof.

The hollow truncated cone-shaped filtering element is preferably formed so as to have the top and bottom portion surfaces thereof which form flat horizontal surfaces, respectively. In other words, a perpendicular cross-sectional view (i.e., vertical cross-sectional view) shows the filtering element as a trapezoid. By forming the filtering element into such a shape, the fitness between the bottom portion of the filtering element and the housing can be improved. Namely, there is increased stability as a result of the bottom portion surface of the filtering element being in flat contact with the inside surface of the housing, and this allows the fixing of the filtering element to the housing to be carried out with ease and reliability using a filling material (potting material).

Further, as the top portion of the filtering element is also formed to be level with the horizontal, there is higher reliability with regards to the seal formed with the filling material. Moreover, this type of filtering element can be produced easily by using an instrument having inclined slits.

When the filtering element is formed from a sheet comprising at least one layer of material made from resinous fiber, the top and bottom portions of the filtering element are preferably heat treated to melt and harden the surfaces thereof. Carrying out this procedure fuses any loose fibers and prevents the occurrence of fraying.

Further, in the filtering apparatus of the present invention, it is preferred that the housing be formed so as to have a roughly circular shaped cross section. Also, it is preferred that the inlet to the housing be formed so as to protrude along a line that is roughly tangential to the inner circumferential surface of the housing, so as to allow the blood flowing into the first space of the housing through the blood inlet1 to form a swirling flow. This swirling flow acts as an anticoagulating means for the blood and makes it possible to further improve the level of bubble separation and removal.

These and other features, objects, and advantages of the present invention will become more apparent upon consideration of the following detailed description of the preferred embodiments with reference to the drawings.

DETAILED DESCRIPTION OF THE PREFERRED EMBODIMENTS

Hereinafter, a detailed description of the preferred embodiments of the present invention will now be given with reference to the accompanying drawings.

Figure 1:
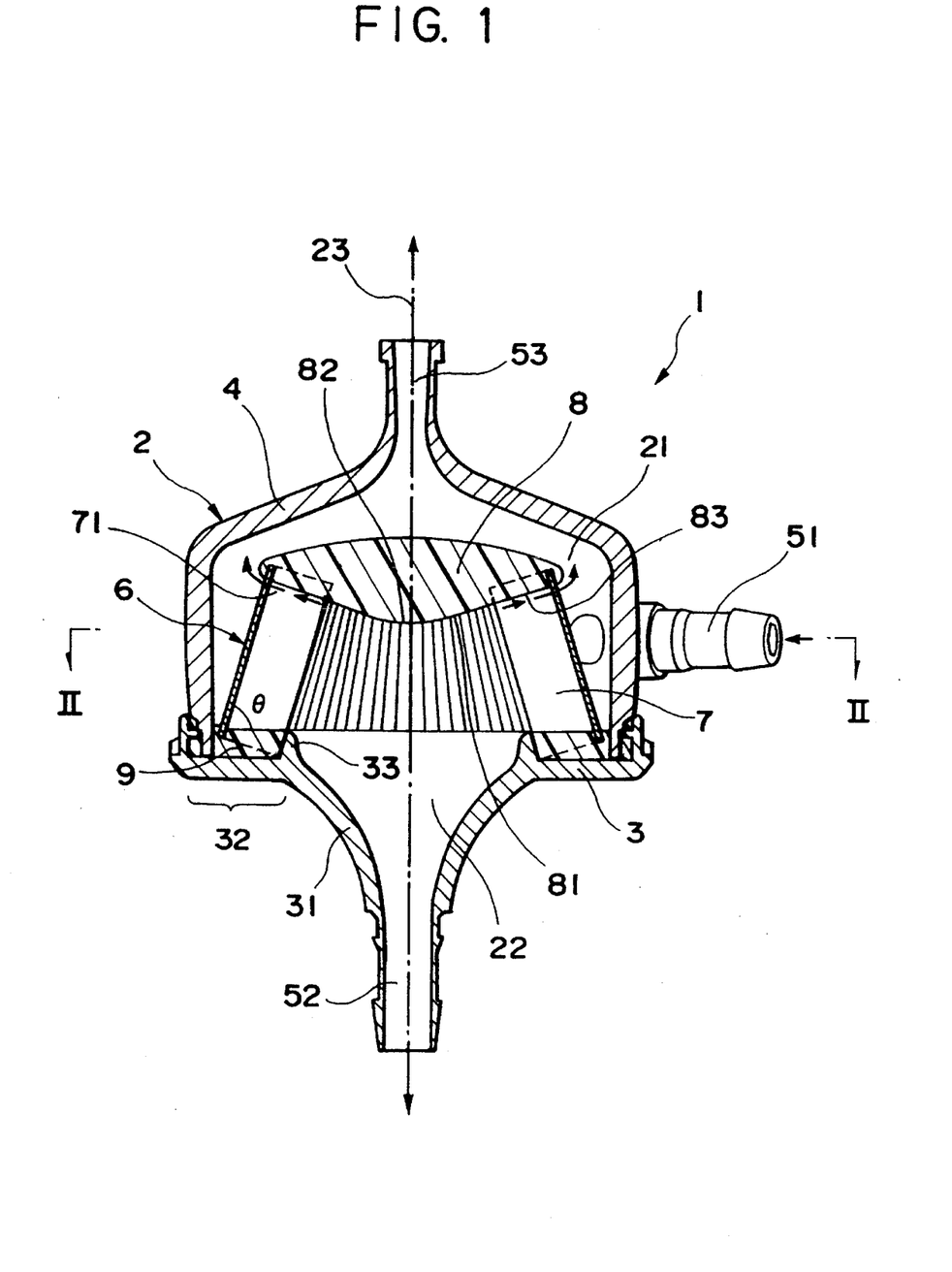
FIG. 1 is a vertical cross-sectional view of a first embodiment of a filtering apparatus according to the present invention.
Figure 2:
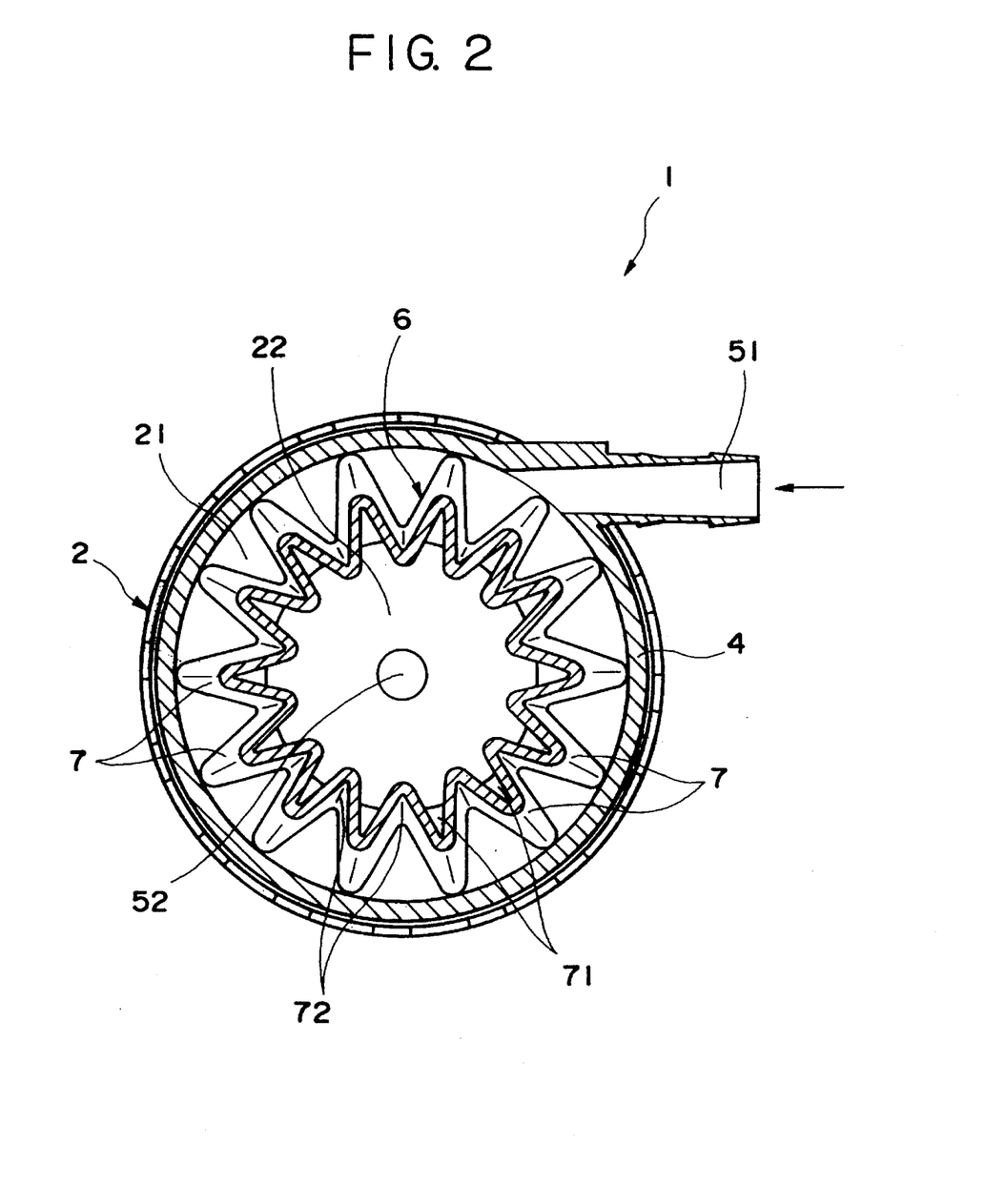
FIG. 2 is a cross-sectional view showing the filtering apparatus of FIG. 1 taken along line II—II thereof.

FIG. 1 shows a vertical cross-sectional view of a filtering apparatus, according to the present invention, that can be used in an blood treatment system, and FIG. 2 is a cross-sectional view taken along line II—II of FIG. 1.

As shown in these drawings, a filtering apparatus 1 of the present invention has a housing 2 comprised of a bottom casing 3 and a cover 4. After being provided with a filtering element 6 described hereinbelow, the bottom casing 3 and the cover 4 are joined together, for example with a threaded fitting means similar to that mentioned in Laid-Open Patent Publication No. 62-84772, and then a filling material 9 described hereinbelow is supplied to this joint portion to form a liquid-tight seal.

The housing 2 has the shape obtained by rotating the cross-sectional shape around a central axis 23. Namely, as is shown in FIG. 2, the horizontal cross-sectional view of the housing 2 roughly forms a circle. In the outer circumferential surface of the cover 4 of the housing 2, there is formed a blood inlet 51 for receiving blood to be treated. This blood inlet 51 is formed so as to protrude along a line that is roughly tangential to the inner circumferential surface of the cover 4. This allows the blood flowing into the housing 2 through the blood inlet 51 to form a swirling flow flowing in one direction along the inner circumferential surface of the cover 4.

As shown in FIG. 1, the inner and outer diameters of the central upper portion of the cover 4 of the housing 2 gradually decrease to form a conical or funnel-like shape that points upwards, the tip of which protrudes to form a vent 53 for discharging gases that are produced when air bubbles are separated and removed from the blood being filtered. Further, even though it is not illustrated in the drawings, the vent 53 is connected to a valve such as a three-way valve for use therewith.

As is also shown in FIG. 1, the inner and outer diameters of the central portion of the bottom casing 3 of the housing 2 gradually decrease to form a funnel-like shape that points downward and defines a blood outflowing section 31, the tip of which protrudes to form a blood outlet 52.

Further, it is preferred that the blood outlet 52 and the vent 53 be formed in alignment with the central axis 23 of the housing 2.

For fixing the filtering element 6, a filtering element fixing portion 32 is formed around the outer circumference of the blood outflowing section 31 of the bottom casing 3. At the boundary between the filtering element fixing portion 32 and the blood outflowing section 31, a rib 33 is formed as a ring-shaped protrusion inside the housing 2. This rib 33 acts as a stopper for the inner ends of the pleats 7 that protrude toward the inside of the filtering element 6, and also acts as a dam for preventing the filling material 9 that is poured into the filtering element fixing portion 32 from overflowing into the blood outflowing section 31.

Examples of materials used to construct the bottom casing 3 and the cover 4 of the housing 2 include polycarbonate, acrylic resin, polyethylene terephthalate, polyethylene, polypropylene, polystyrene, polyvinyl chloride, acrylic-styrene copolymers, acrylic-butadiene-styrene copolymers, and the like. Preferably, a transparent or semi-transparent material is used so as to allow the visual inspection of the inside of the housing.

The filtering element 6 is provided inside the housing 2 for filtering air bubbles and foreign substances that have been mixed with the blood. By the provision of the filtering element 6, the inside of the housing 2 is partitioned into a first space 21 defined by the space outside the filtering element 6 and a second space 22 defined by the space inside the filtering element 6. The blood inlet 51 and the vent 53 communicate with the first space 21, and the blood outlet 52 communicates with the second space 22.

Now, a detailed explanation will be given below on the structure of the filtering element 6.

The filtering element 6 is made by folding a porous material to form a plurality of pleats and is then positioned so as to form a cylindrical shape with each pleat 7 radiating outwardly therefrom. The top portion opening of the cylindrical-shaped filtering element 6 is then sealed by the application of a filling material 8.

In the present embodiment, the filtering element 6 forms a hollow truncated conical shape, with the outermost diameter thereof gradually increasing from top to bottom. By forming the filtering element 6 into this shape, a satisfactorily smooth flow of both the blood flowing into the first space 21 and the blood forming a swirling flow within the first space 21 is achieved without having to enlarge the capacity of the housing 2, or more specifically stated, without having to increase the quantity of priming fluid. As a result, the rate of separation and removal of air bubbles and foreign substances is increased, and in addition to that, it becomes possible to reduce any losses in pressure and to suppress the occurrence of hemolysis.

As a porous material used for constructing the pleated filtering element 6, examples include meshes, nettings, foams, woven fabrics, non-woven fabrics, and combinations thereof, but any similar type of material can be used thereto. In particular, meshes, nettings, woven fabrics, non-woven fabrics, and the like made from resinous fibers are preferably used to form a laminated sheet composed of one or more layers. One example of such a sheet would be a screen mesh made from polypropylene or polyester which is then sandwiched with nettings made from polypropylene or polyester. Further, the porous material used for the mesh and nettings is preferably selected to have a minimum pore diameter within the range of 20 microns–200 microns, and in particular, the range 20 microns–60 microns is preferred.

In the present invention, there is a distinctive feature with regards to the shape of the filling material 8 used to seal the opening at the top of the filtering element 6. Namely, as is shown in FIG. 1, the filling material 8 has a bottom surface 81 that faces towards the second space 22, and this bottom surface 81 has a central portion 82 which protrudes into the second space 22. Extending from the central portion 82 to the outer circumference of the filling material 8 is a pleat intersecting portion 83 which intersects each pleat 7, and this intersecting portion 83 is formed so as to have a predetermined inclination angle relative to the horizontal (the lateral direction in FIG. 1).

By forming the bottom surface 81 of the filling material 8 with the shape described above, it becomes easier to remove air bubbles that appear in the second space 22 during priming and air bubbles that enter into the troughs 72 between the pleats 7 when blood is being treated.

In this regard, there is no particular restriction to the inclination angle of the pleat intersecting portion 83, relative to the horizontal, but in order to effectively exhibit the effects mentioned above, an average of 5° or more is preferred, and in particular, it is preferred that the angle lie within the range of 10°–60°.

The filling material 8 may be composed from high polymer materials, examples of which include polyurethane, silicone, epoxy resin, polyolefine such as polyethylene, polypropylene and ethylene-vinyl acetate copolymers and the like, and various rubber materials. Of these high polymer materials, polyurethane, silicone, and epoxy resin are preferred.

While there are no specific restrictions as to the dimensions of the filtering element 6, an example of a appropriate range is given below in Table 1.

TABLE 1

|  | Small Children | Adults |
|---|---|---|
| Thickness of porous material | 3 mm ≦ (1 mm ≦) | 3 mm ≦ (1 mm ≦) |
| Outer diameter of the bottom of the filtering element | 20–80 mm (30–50 mm) | 30–100 mm (40–70 mm) |
| Outer diameter of the top of the filtering element | 10–60 mm (20–40 mm) | 10–80 mm (30–60 mm) |
| Internal diameter of the bottom of the filtering element | 10–70 mm (20–40 mm) | 20–90 mm (30–60 mm) |
| Internal diameter of the top of the filtering element | 5–50 mm (10–30 mm) | 5–70 mm (20–60 mm) |
| Height of the filtering element | 8–40 mm (10–30 mm) | 20–100 mm (40–80 mm) |
| Number of pleats | 15–50 (20–40) | 15–50 (20–40) |
| Effective surface area of the filtering element | 50–300 cm$^2$ (100–200 cm$^2$) | 200–1000 cm$^2$ (400–800 cm$^2$) |
| Average inclination angle θ of the side surface of the filtering element | 45°–85° (60°–75°) | 45°–85° (60°–75°) |

*Values within parentheses are especially preferred

This type of filtering element 6 can be manufactured, for example, by methods like the following.

First, a porous material is folded in such a way as to have a plurality of pleats, and then this pleated sheet is curled so as to form a hollow cylinder with the pleats radiating outwardly. Next, a filling material 8 is poured on top of this cylindrically shaped porous material. At this time, it is alright for the bottom surface 81 to be horizontal.

Before the filling material 8 completely hardens, the bottom portion of the filtering element 6 is spread or expanded outwardly, for example, by the insertion of a specially molded object. By this action, the filtering element 6 is made to take on a hollow truncated conical shape, which forces the bottom surface 81 to form the shape previously described. Then, after the filling material 8 has been thoroughly hardened, the molded object is removed to obtain a filtering element 6 like that shown in the drawings.

As the conical shape of the filtering element 6 and the special shape of the bottom surface 81 of the filling material 8 can be easily obtained with manufacturing methods like that just described, excellent reproducibility is achieved during mass production.

For fixing thus formed filtering element 6 to the housing 2, the filling material 9 is first poured into the filtering element fixing portion 32 of the bottom casing 3. Then, the bottom portion of the filtering element 6 is positioned in the filtering element fixing portion 32 in such a manner that the bottom portion is immersed in the filling material 9 and the inner ends of the pleats that project towards the inside of the filtering element 6 are engaged with the rib 33. The filling material 9 is then hardened to secure the filtering element 6 at that place. When the filtering element 6 is being fixed in this manner, it is preferred that the central axis of the filtering element 6 be aligned with or in close proximity to the axis 23 of the housing 2.

Figure 3:
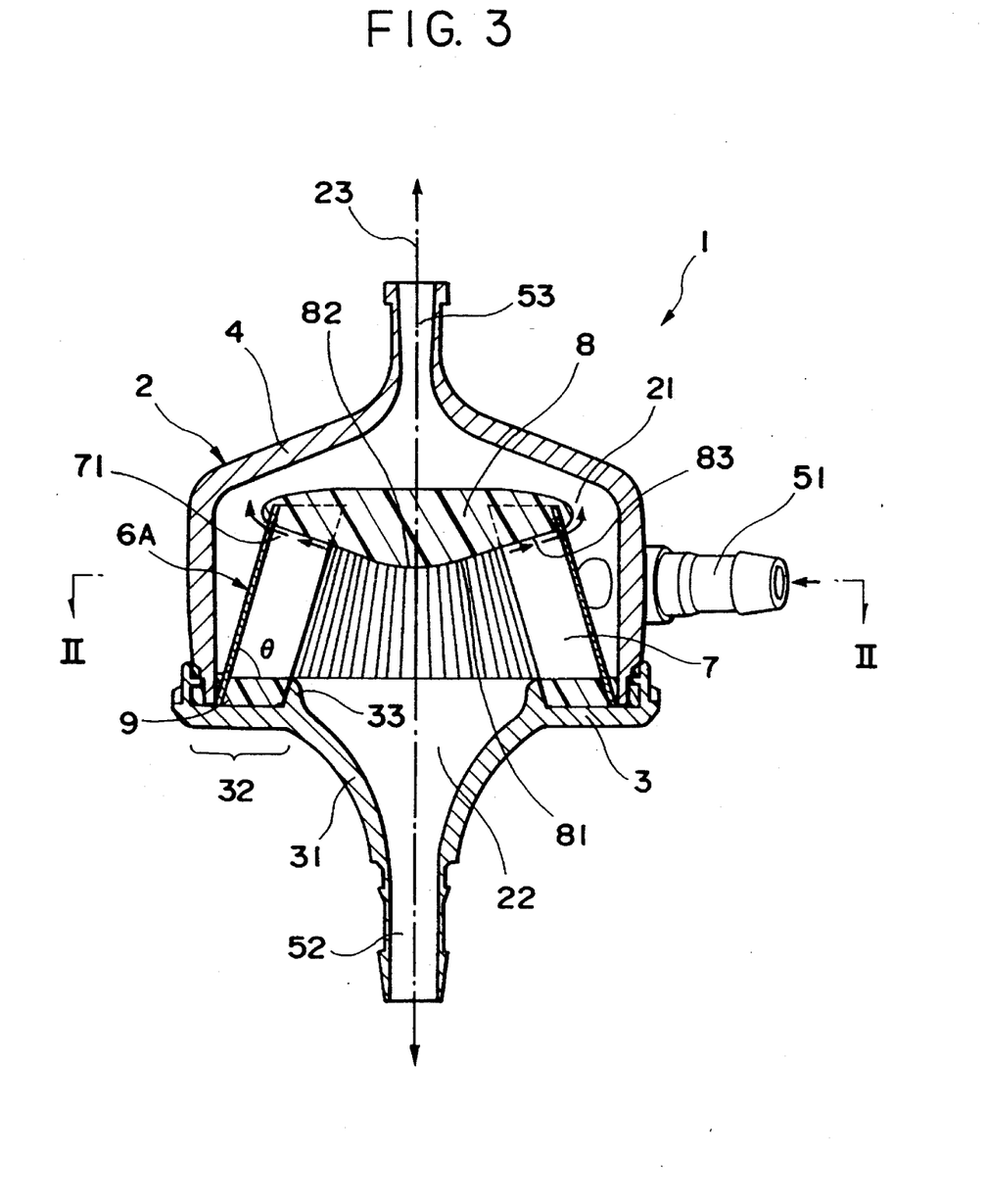
FIG. 3 is a vertical cross-sectional view of a second embodiment of a filtering apparatus according to the present invention.

A vertical cross-sectional view of a second embodiment of a filtering apparatus according to the present invention is shown in FIG. 3. Since the second embodiment is essentially the same as the first embodiment, except for the structure of the filtering element 6A, the same elements or components will be designated by the same numbers. For this reason, a detailed description of these elements is not considered to be necessary and is therefore omitted.

The difference between the filtering element 6A of the second embodiment and the filtering element 6 of the first embodiment lies in the feature that when the filtering element 6A is formed into its respective hollow truncated cone shape and positioned within the housing 2, the top and bottom portion surfaces thereof form flat horizontal surfaces, respectively (relative to the horizontal in FIG. 3). In other words, when the hollow truncated conically shaped filtering element 6A is positioned within the housing 2, a perpendicular cross-sectional view (i.e., vertical cross-sectional view) shows the filtering element 6A taking on the shape of a trapezoid with horizontally flat top and bottom surfaces. By forming the filtering element 6A into such a shape, the fitness between the bottom portion of the filtering element 6A and the housing 2 can be improved. Namely, there is increased stability as a result of the bottom portion surface of the filtering element 6A being in flat contact with the upper surface of the filtering element fixing portion 32 of the bottom casing 3 of the housing 2, and this allows the fixing of the filtering element 6A to the bottom casing 3 to be carried out with ease and reliability using the filling material 9. Further, as the top portion of the filtering element 6A is also formed to be level with the horizontal, there is further advantage of a higher reliability with regards to the seal formed with the filling material 8. Moreover, since the top or upper portion of the filling material 8 forms a horizontal or essentially horizontal shape, there is hardly any occurrence of the protrusion into the first space 21 of filling material 8 that seals the opening at the top portion of the filtering element 6A. Consequently, use of the filling material 8 can be economized.

Now, described below is an example of a manufacturing method for producing filtering elements like the filtering element 6A.

Figure 4:
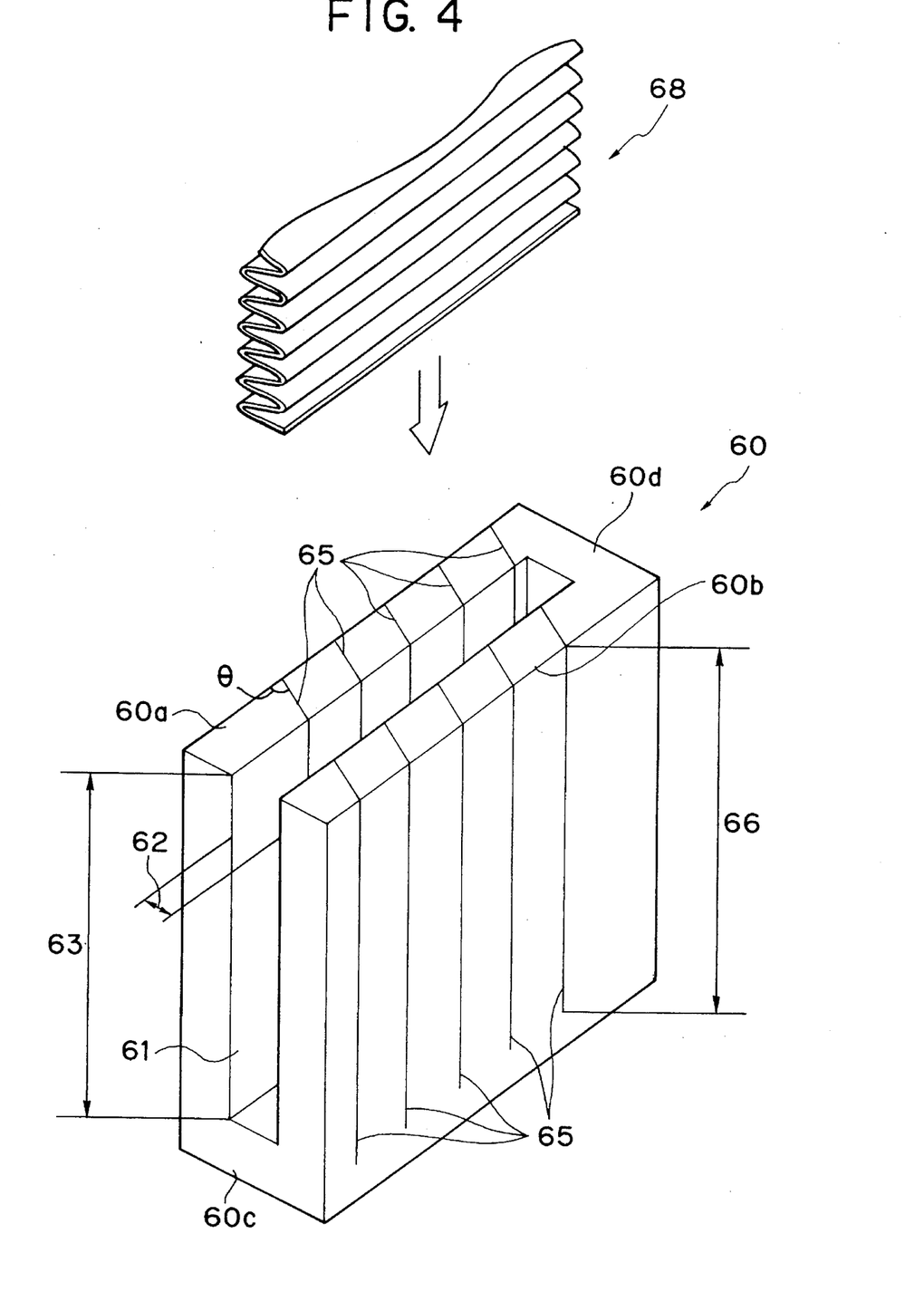
FIG. 4 is a perspective view of an instrument used for making the filtering material employed in the second embodiment of the filtering apparatus.

FIG. 4 shows a perspective view of an instrument 60 used in producing the filtering element 6A. The instrument 60 comprises side walls 60a, 60b positioned parallel to each other at a prescribed spacing, a base portion 60c connected to the bottom portions of the side walls 60a, 60b, and a connecting portion 60d connected to one of the two pairs of side ends of the side walls 60a, 60b. These elements are joined together so as to form a substantially rectangular parallelopiped block which forms a U-shaped cross section when viewed from the side of the open ends of the side walls 60a, 60b (i.e., the pair of side ends opposite to that where the connecting portion 60d is connected), and this U-shaped portion defines a slot 61 that extends from the open end side all the way to the connecting portion 60d.

A porous material 68 which has been folded to form pleats is to be inserted into the slot 61, and then cut into the size appropriate to make the filtering element 6A. The width 62 of the slot 61 is roughly the same size as the height between the peak and the trough of each pleat of the pleated porous material 68. Further, the depth 63 of the slot 61 is roughly the same or slightly larger than the precut length of the pleated porous material along the direction of the repeating pleats thereof.

Further, formed in the side walls 60a, 60b are a plurality of slits 65 (five slits in this embodiment) that pass through the slot 61 along equally spaced parallel planes. Each of the slits 65 are formed so as to have an inclination angle θ (θ<90°) with respect to the outside surface of the side wall 60a, and this inclination angle θ is equal to the inclination angle θ of the outer surface of the truncated conically shaped filtering element 6A with respect to the horizontal when positioned within the housing 2. Furthermore, the spacing between adjacent slits 65 is the same as the length from top to bottom of the outer surface of the truncated conically shaped filtering element (i.e., the length of each pleat of the filtering element 6A). In this way, the portion of the slot 61 defined by adjacent slits 65 forms a parallelogram which is nearly identical to the shape of the end portion of the porous material that can be used to make the filtering element 6A.

The slits 65 are formed so as to extend from the top surfaces of the side walls 60a, 60b to the base portion 60c, such that the slit depth 66 is greater than the slot depth 63. As for the width of the slits 65, an appropriate setting is selected to allow a cutter (not shown in the drawings) to pass through the slits and cut the porous material 68 that has been inserted into the slot 61.

Accordingly, after the pleated porous material 68 has been placed inside the slot 61, cutters are inserted at the top of the slits 65 and forced down to the bottom end of the slits to cut the porous material 68 into a plurality of sheets having prescribed shapes for constructing the filtering element 6A. Namely, it is possible to obtain a plurality of pleated porous material sheets having parallelogram-shaped end portions. Now, since the instrument 60 (as shown in FIG. 4) is provided with five slits, the pleated porous material 68 is cut into a total of six sheets. However, the two outermost side sheets are set aside, and only the inner four sheets are used for making the filtering element 6A.

Here it should be mentioned that the filtering element 6 of the first embodiment, as shown in FIG. 1, can also be made with the instrument 60 of FIG. 4. In this case, the slits are formed at right angles to the side walls 60a, 60b (i.e., θ=90°).

After the above steps have been carried out, the matching end portions of the cut porous material sheets are fused together to form a cylindrical shape. Namely, the porous material that has been folded to provide a plurality of pleats thereto, is formed into a cylindrical shape with the pleats radiating outwardly. Next, a filling material 8 is supplied to the top portion of the cylindrically shaped porous material, in the same way as was done for the first embodiment. At this time, it is alright for the bottom surface 81 of the filling material 8 to be horizontal.

Before the filling material 8 completely hardens, the bottom portion of the filtering element 6A is spread outwardly, for example, by the insertion of a specially molded object. By this action, the filtering element 6A is made to take on a truncated conical shape, which forces the bottom surface 81 of the filling material 8 to form the protruding shape previously described. Then after the filling material 8 has been thoroughly hardened, the molded object is removed to obtain a filtering element 6A like that shown in the drawings. As was mentioned previously mentioned, the truncated conically shaped filtering element 6A obtained in this way is made from porous material sheets that have been cut in the instrument 60 to give each pleat thereof a parallelogram shape, so that the top and bottom portions of the hollow truncated conically shaped filtering element 6A form flat surfaces that are level with the horizontal (when mounted in the housing 2). In other words, a cross section of the completed filtering element 6A forms a trapezoid.

As was previous mentioned above, the filtering elements 6, 6A are made from meshes, nets, woven fabrics (plain weave) and the like that are formed by a plurality of layers made from the same or different materials formed of resinous fibers. Consequently, when the filtering elements 6, 6A are formed from the porous material that has been cut into the shape by the cutters described above for the instrument 60. this may give rise to fraying at the cut end surfaces of the filtering elements 6, 6A, which is the primary cause of foreign substances. For this reason, after the matching end portions are fused or otherwise bonded together to form the cylindrical shape, and before applying the filling material 8, a heat treatment is preferably carried out to melt and harden the loose resinous fibers at the cut surfaces of the top and bottom portions of the filtering element 6, 6A. By carrying out such heat treatment, the ends of the loose resinous fibers are fused together, and this prevents the occurrence of fraying. An example of this sort of heat treatment is illustrated in FIG. 5.

Figure 5:
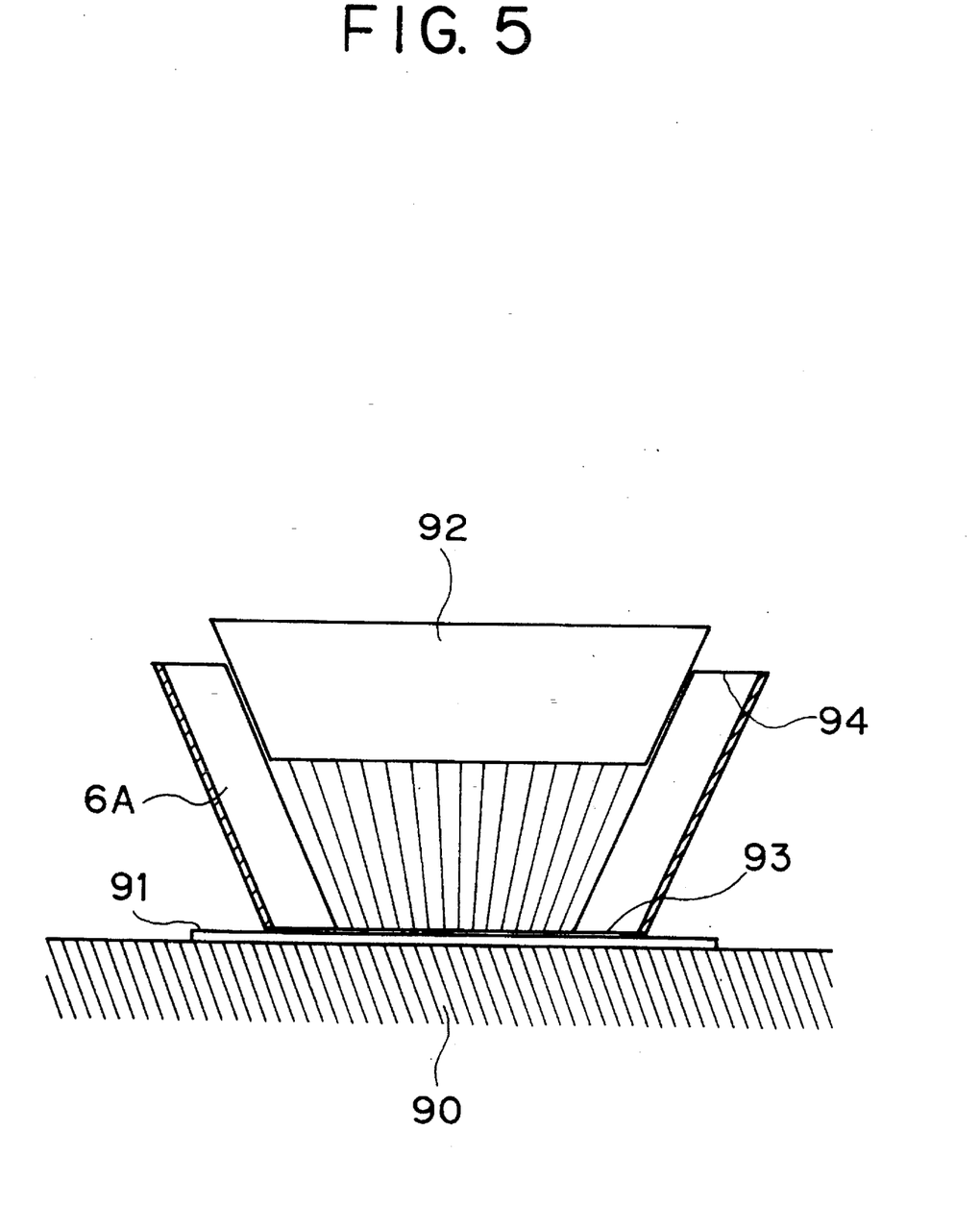
FIG. 5 is a cross-sectional view showing the filtering material of the second embodiment undergoing heat treatment.

FIG. 5 shows a cross-sectional view of the filtering element 6A of FIG. 3 undergoing the heat treatment described above. As shown in FIG. 5, on top of a hot plate 90 that is heated to a temperature above the melting point of the porous material, there is placed a removable teflon sheet 91 for easy removal from the hot plate 90. Placed on the top of the teflon sheet 91 is the porous material that has been changed from the cylindrical shape to the hollow final truncated cortically shaped filtering element 6A, and the top portion of the filtering element 6A is pushed against the teflon sheet with maintaining the truncated-cone shape. At this time, it is preferred that the truncated-cone shape of the filtering element 6A be maintained by the insertion of a molded object 92 into the bottom portion thereof, as this is one easy way of maintaining such a shape. Further, since this causes the top portion of the filtering element 6A to be maintained as a flat surface, there is uniform melting at that surface. After sufficient melting has occurred, the porous material is removed from the hot plate 90 with the teflon sheet 91 stuck to the top portion of the filtering element 6A. Then, as soon as the resinous fibers at the top portion of the filtering element 6A have sufficiently cooled, the teflon sheet 91 is removed to reveal a fused top portion 93. This type of heat treatment can also be performed on the bottom portion 94 of the filtering element 6A, which then eliminates the possibility that fraying will occur with the resinous fibers that comprise the filtering element 6A.

Needless to say, the heat treatment described above for treating porous material made from resinous fiber can be performed on the filtering element 6 of the first embodiment. In this case, such a heat treatment would be performed on the cylindrically shaped porous material before it is spread to form the truncated conically shaped filtering element 6.

Further, it should be noted that the melting and hardening of the top portion 93 and the bottom portion 94 need not be limited to the method explained above using the hot plate shown in FIG. 5. Examples of other methods include the use of fusing techniques utilizing high frequency waves or ultrasonic waves.

Figure 6:
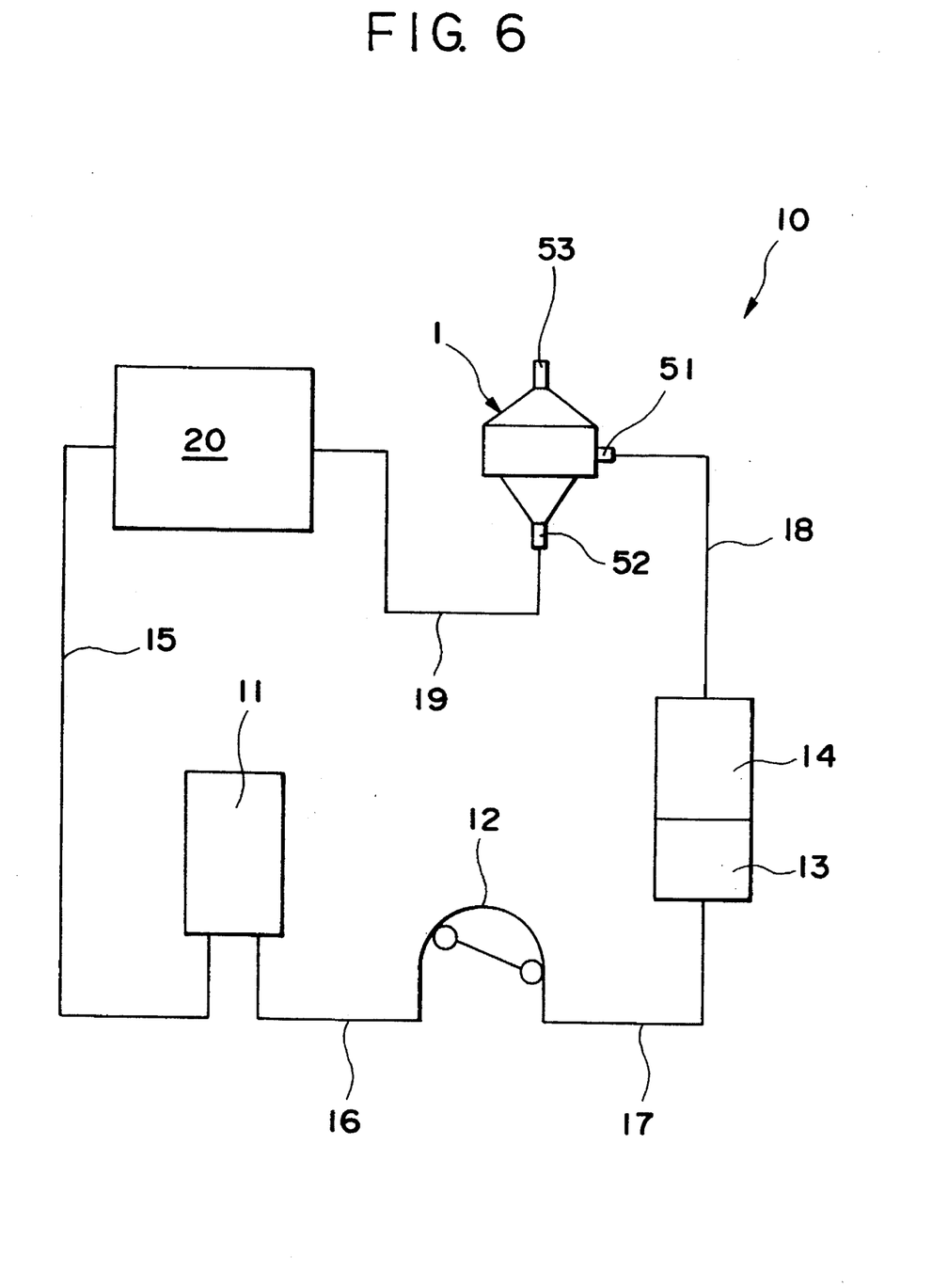
FIG. 6 illustrates a blood treatment system incorporating the filtering apparatus of the present invention.

FIG. 6 shows a blood treatment system 10 mounted with the filtering apparatus 1 of the present invention. The blood treatment system 10 comprises a blood reservoir 11, a roller pump 12, a heat exchanger 13, an artificial lung 14, the filtering apparatus 1, a first tube 15 connecting a vein of a patient 20 to the blood reservoir 11, a second tube 16 connecting the blood reservoir 11 with the roller pump 12, a third tube 17 connecting the roller pump 12 with the heat exchanger 13, a fourth tube 18 connecting the blood outlet of the artificial lung 14 with the blood inlet 51 of the filtering apparatus 1, and a fifth tube 19 connecting the blood outlet 52 of the filtering apparatus 1 to an artery of the patient 20.

During priming and blood treatment with the blood treatment system, the filtering apparatus 1 is mounted within the blood treatment system 10 in a position that aligns the axis 23 of the filtering apparatus 1 in the vertical direction.

Next, the operation of the filtering apparatus 1 will be described below.

Priming Operation

A priming fluid, such as saline solution, is introduced through the fifth tube 19 into the inside of the housing 2 from the blood outlet 52 thereof. Intermixed with the priming fluid are tiny bubbles that float up within the second space 22 until they arrive at the bottom surface 81 of the first filling material 8. At this time, since the bottom surface 81 has a central portion 82 that protrudes downwardly so that the bottom surface 81 slants upwardly along the direction toward the outer circumference of the bottom surface 81 (as was previously described above), buoyancy causes the bubbles to move upwardly along this slanting surface until they enter the inside of the peaks 71 of the pleats 7 that radiate outwardly. Then the difference in pressure between the second space 22 and the first space 21 forces the bubbles to migrate through the pores of the filtering element 6 (6A) to enter into the first space 21. After these bubbles pass into the first space 21, they continue to rise until they reach the top of the cover 4, where they are discharged to the outside of the housing 2 through the vent 53.

As no bubbles remain in the vicinity of the bottom surface 81 of the first filling material 8, there is a substantial improvement with regards to the bubble separation or exclusion capability. Moreover, in obtaining this improvement, it is not necessary for the volume of the housing 2 to be greater than that used in the prior art, nor are any changes in shape are required. Accordingly, an increase in the amount of priming fluid is not needed.

Blood Treatment

Blood taken from the vein of the patient 20 is transferred through the first tube 15 to the blood reservoir 11 and once reserved therein. Then the roller pump 12 is actuated to transfer the blood, through the second and third tubes 16, 17, to the heat exchanger 13, where the blood undergoes heating or cooling. Upon exiting the heat exchanger, the blood flows into the artificial lung 14 where it is oxygenated and carbon dioxide contained therein is removed. The blood then flows through the fourth tube 18 and enters the filtering apparatus 1 via blood inlet 51.

Since the blood enters the housing 2 through the blood inlet 51, it creates a swirling flow within the first space 21. In the case where there are bubbles intermixed with the blood, buoyancy forces these bubbles to float up towards the top of the covering 4 while they move with the swirling flow of blood. Further, since there is a centrifugal force acting on these light-mass bubbles, they tend to collect in the central portion of the swirling flow, and this helps to force the bubbles to follow the surface of the upper portion of the cover 4 as they float upwardly. Upon reaching the vent 53, the bubbles are discharged to the outside of the housing 2. Furthermore, the swirling flow of blood is very effective in preventing the blood from stagnating or coagulating inside the housing 2.

At this time, any bubbles that do not readily float up to the top portion of the cover 4 will enter the troughs 72 between the pleats 7 (i.e., the gaps between adjacent pleats). At the back portion of the these troughs 72, the bubbles float up until they reach the bottom surface 81 of the filling material 8 at the pleat intersecting portion 83 thereof. Now, as was previously explained above, since the bottom surface 81 is inclined, the bubbles float up along this inclined surface and exit the troughs 72. Accordingly, it is possible to prevent bubbles from remaining inside the troughs 72.

Furthermore, any tiny bubbles that manage to pass through the pores of the filtering element 6 (6A) and enter the second space 22 will float up in the same manner as was described above for the situation that arises during priming. These bubbles that pass into the second space 22 will float up until they reach the bottom surface 81, where they will be forced by buoyancy to float up along the inclined bottom surface 81 until they reach the top portions of the inside portions 71 of the pleats 7 that radiate outwardly. Then, the bubbles, from there, pass back through the pores of the filtering element 6 to enter into the first space 21 and then float up therein, to be discharged through the vent 53.

The filtered blood that flows into the second space 22 then passes through the blood outflow section 31 and the blood outlet 52 to be returned to the patient 20 through the fifth tube 19 connected to an artery of the patient 20.

As explained above, since any bubbles that enter the troughs 72 or the inside portions 71 of the pleats 7 can be effectively removed and discharged out of the housing 2, there is a substantial increase in the efficiency of bubble separation and removal from the blood. Moreover, in obtaining this improvement in blood separation and removal, it is not necessary for the volume of the housing 2 to be greater than that used in the prior art, nor are any changes in shape required. Accordingly, an increase in the amount of priming fluid is not needed.

It is to be noted that the use of the apparatus according to the present invention is not limited to the blood filtering and bubble removal apparatuses shown in FIGS. 1 and 3, and can be utilized for other medical or industrial purposes.

Furthermore, the treatment of fluids in accordance with the present invention is not limited to the above-described treatment of blood, and can be used to treat other body fluids such as plasma, or it can be used to treat fluids in general.

Next, specific example embodiments of the filtering apparatus of the present invention will be described in detail below.

Example Embodiment 1

This example embodiment of a filtering apparatus has been constructed to correspond to the first embodiment shown in FIGS. 1 and 2, with the filtering element 6 being constructed in accordance with the manufacturing method previously described above. The specifications of this example embodiment are given below.

| | |
|---|---|
| Housing Material: | Polycarbonate |
| Inside Diameter of Blood Inlet: | 6.0 mm |
| Inside Diameter of Blood Outlet: | 6.0 mm |
| Inside Diameter of Vent: | 4.3 mm |
| Construction of Porous Material: | A polyester screen mesh (Pore Diameter: 32 microns) sandwiched between polypropylene nets (Pore Diameter: 500 microns) |
| Thickness of Porous Material: | 1.00 mm |
| Bottom Portion Outer Diameter of Filter Element: | 60 mm |
| Top Portion | 34 mm |
| Outer Diameter of Filter Element: Bottom Portion | 44 mm |
| Inner Diameter of Filter Element: Top Portion | 18 mm |
| Inner Diameter of Filter Element: | 22 mm |
| Height of Filter Element: | |
| No. of Pleats: | 30 |
| Effective Surface Area of Filter Element: | 200 cm² |
| Filling Material: | Polyurethane |
| Average Inclination Angle of Bottom Surface of Filling Material (Pleat Intersecting Portion): | 15° with respect to the horizontal |
| Volume of Priming Fluid: | 40 ml |

Example Embodiment 2

This example embodiment of a filtering apparatus has been constructed to correspond to the second embodiment shown in FIG. 3, with the filtering element 6A being constructed in accordance with the manufacturing method previously described above.

In this example embodiment, the instrument 60 has been used to cut the filtering element 6A into a predetermined shape. The specifications of the instrument 60 are given below.

| | |
|---|---|
| Width 62 of Slot 61: | 8 mm |
| Depth 63 of Slot 61: | Approximately 8 cm |
| Angle θ of Slits 65: | 70° |
| Spacing between Slits: | 24.5 mm |

Further, the top and bottom portions of the filtering element 6A underwent heat treatment on the hot plate at a temperature of 250° C. for a period 10 seconds. The specifications of the filtering apparatus mounted with this filtering element 6A are given below.

| | |
|---|---|
| Housing Material: | Polycarbonate |
| Inside Diameter of Blood Inlet: | 6.0 mm |
| Inside Diameter of Blood Outlet: | 6.0 mm |
| Inside Diameter of Vent: | 4.3 mm |
| Construction of Porous Material: | A polyester screen mesh (Pore Diameter: 32 microns) sandwiched between polyethylene terephthalate nets (Pore Diameter: 450 microns) |
| Thickness of Porous Material: | 1.0 mm |
| Bottom Portion Outer Diameter of Filter Element: | 50 mm |
| Top Portion Outer Diameter of Filter Element: | 35 mm |
| Bottom Portion Inner Diameter of Filter Element: | 35 mm |
| Top Portion Inner Diameter of Filter Element: | 18 mm |
| Height of Filter Element: | 23 mm |

| | |
|---|---|
| No. of Pleats: | 31 |
| Effective Surface Area of Filter Element: | 100 cm² |
| Filling Material: | Polyurethane |
| Average Inclination Angle of Bottom Surface of Filling Material (Pleat Intersecting Portion): | 15° with respect to the horizontal |
| Volume of Priming Fluid: | 40 ml |

Comparative Example 1

Except for the the filtering element, this comparative example was constructed to be roughly the same as Example Embodiment 1. The specifications of this comparative example are given below.

| | |
|---|---|
| Construction of Porous Material: | Same as Example Embodiment 1 |
| Thickness of Porous Material: | Same as Example Embodiment 1 |
| Bottom Portion Outer Diameter of Filter Element: | 47 mm |
| Top Portion Outer Diameter of Filter Element: | 47 mm |
| Bottom Portion Inner Diameter of Filter Element: | 31 mm |
| Top Portion Inner Diameter of Filter Element: | 31 mm |
| Height of Filter Element: | Same as Example Embodiment 1 |
| No. of Pleats: | Same as Example Embodiment 1 |
| Effective Surface Area of Filter Element: | Same as Example Embodiment 1 |
| Filling Material: | Same as Example Embodiment 1 |
| Bottom Surface of Filling Material: | Horizontal |
| Volume of Priming Fluid: | 41 ml (Approximately the same as Example Embodiment 1) |

Comparative Example 2

Except for an increase in the size of the filtering element and an increase in the casing volume, the filtering apparatus of this comparative example is the same as Example Embodiment 1. The specifications of this comparative example are given below.

| | |
|---|---|
| Construction of Porous Material: | Same as Example Embodiment 1 |
| Thickness of Porous Material: | Same as Example Embodiment 1 |
| Bottom Portion Outer Diameter of Filter Element: | 60 mm |
| Top Portion Outer Diameter of Filter Element: | 60 mm |
| Bottom Portion Inner Diameter of Filter Element: | 44 mm |
| Top Portion Inner Diameter of Filter Element: | 44 mm |
| Height of Filter Element: | 42 mm |
| No. of Pleats: | Same as Example Embodiment 1 |
| Effective Surface Area of Filter Element: | 400 cm² (Twice that for Example Embodiment 1) |
| Filling Material: | Same as Example Embodiment 1 |
| Bottom Surface of Filling Material: | Horizontal |
| Volume of Priming Fluid: | 110 ml (2.75 times that of Example Embodiment 1) |

The experiments described below were conducted using Example Embodiment 1, Example Embodiment 2, and Comparative Examples 1 and 2.

Experiment 1

A priming fluid (saline solution) containing tiny bubbles intermixed therewith was supplied to the filtering apparatus of each of Example Embodiment 1, Example Embodiment 2, and Comparative Examples 1 and 2 through their respective blood outlets to fill up their respective housings. Then, while maintaining this condition, each filtering element was visually inspected for the presence of bubbles adhering thereto in order to evaluate the level of bubble separation and removal.

In the filtering apparatuses of Example Embodiment 1 and Example Embodiment 2, extremely small bubbles were observed to be adhering in the vicinity of the top portion of the filtering element, but these were easily removed by lightly shaking the filtering apparatus.

However, in both the filtering apparatuses of Comparative Examples 1 and 2, many bubbles were observed near the vicinity of the top portion of the filtering element, especially on the inside of the peak portion of each pleat (i.e., on the inside of the filtering element).

The above experiment confirms the superior bubble separation and removal capabilities of the filtering apparatus of Example Embodiment 1 and Example Embodiment 2 over that of Comparative Examples 1 and 2.

Next, a blood treatment experiment was conducted with the filtering apparatuses of each of Example Embodiment 1, Example Embodiment 2, and Comparative Examples 1 and 2.

Experiment 2

Cow blood at 37° C. (Hematocrit value: Ht=34.2%) was supplied (after priming) at a flow rate of 2500 ml/min to the filtering apparatuses of each of Example Embodiment 1, Example Embodiment 2, and Comparative Examples 1 and 2, through their respective blood inlets. While this flow rate was maintained, 10 ml of air was injected with a syringe into the blood supply line (i.e., an air shot), and then precisely one minute later a bubble detection apparatus was used to measure the maximum diameter of any bubbles remaining in the blood as it exited each filtering apparatus through their respective blood outlets. These results are indicated in Table 2 below.

TABLE 2

|  | Filtering Element Shape | Bottom Surface Shape of Filling Material | Volume of Priming Fluid | Maximum Bubble Diameter Upon Exiting Outlet |
|---|---|---|---|---|
| Example 1 | Hollow Cone | 15° Inclination | 40 ml | 50 microns |
| Example 2 | Hollow Cone | 20° Inclination | 40 ml | 50 microns |
| Compar. 1 | Cylinder | Horizontal | 41 ml | 80 microns |
| Compar. 2 | Cylinder | Horizontal | 110 ml | 70 microns |

As indicated in Table 2 above, the maximum diameters of the air bubbles that exited through the blood outlets of the filtering apparatuses of Example Embodiments 1 and 2 were relative small compared to the values obtained for Comparative Examples 1 and 2. Accordingly, this confirms the superior capability of the present invention with regards to bubble separation and removal when blood is being treated.

When making comparisons using the data in Table 2, it is observed that the bubble removal capability of the filtering apparatus of Comparative Example 2 is only slightly inferior to the capability obtained by the filtering apparatuses of Example Embodiment 1 and Example Embodiment 2. However, the filtering apparatus of Comparative Example 2 requires a marked increase in the volume of priming fluid. As for the filtering apparatus of Comparative Example 1, even though it does not require an increase in the volume of priming fluid, it is nonetheless inferior to the apparatuses of Example Embodiment 1 and Example Embodiment 2 with regards to bubble separation and removal.

While the present invention has been described in detail with reference to specific embodiments, it is to be understood that the present invention is not limited to such embodiments, and that various changes in form and details can be made therein without departing from the spirit and scope of the invention as defined by the appended claims.

What is claimed is:

1. A filtering apparatus, comprising:
   a housing formed with an inlet through which a fluid to be treated flows into the housing and an outlet through which treated fluid drains out of the housing, said housing also being formed with a vent;
   a filtering element provided inside said housing to partition the inside of said housing into a first space that communicates with said inlet and a second space that communicates with said outlet, said filtering element being made from a porous material that has been folded to form a plurality of pleats and formed so as to have a substantially cylindrical shape with the pleats radiating outwardly, the cylindrically shaped filtering element having a bottom portion and a top portion provided with an opening;
   a filling material for sealing the opening of the top portion of said filtering element with the top portion of the filtering element being embedded in said filling material, said filling material having a lower surface that is positioned at the side of said second space of said housing and an outer peripheral portion, said lower surface having a central portion that protrudes into said second space with said lower surface possessing an upwardly inclined shape, said upwardly inclined lower surface of said filling material extending from the central portion to the outer peripheral portion so that the upwardly inclined lower surface intersects said pleats of said filtering element.

2. The filtering apparatus of claim 1, wherein the outermost diameter of said filtering element gradually increase in the direction from the top portion of said filtering element to the bottom portion thereof.

3. The filtering apparatus of claim 2, wherein the bottom portion of said filtering element is stretched apart after the opening of the top portion of said filtering element is sealed with the filling material.

4. The filtering apparatus of claim 2, wherein the top and bottom portions of said filtering element are formed as flat surfaces, such that a vertical cross section of said filtering element forms a substantially trapezoidal shape.

5. The filtering apparatus of claim 2, wherein said porous material is formed from one or more layers of resinous fiber.

6. The filtering apparatus of claim 5, wherein the top and bottom portions of said filtering element are fused and hardened.

7. The filtering apparatus of claim 1, wherein said housing is formed so that a horizontal cross section thereof forms a substantially circular shape, and said filtering element being concentrically arranged within said housing.

8. The filtering apparatus of claim 7, wherein said inlet is formed so as to protrude along a line that is generally tangential to the inner circumferential surface of said housing so as to allow the fluid flowing into the housing through the inlet to create a swirling flow within said first space.

9. A filtering device for use in a filtering apparatus having a housing formed with an inlet through which a fluid to be treated flows into the housing and an outlet through which treated fluid drains out of the housing, said filtering device comprising a filtering element adapted to be disposed inside the housing to partition the inside of the housing into a first space that communicates with the inlet and a second space that communicates with the outlet, and said filtering element being made from a porous material that has been folded to form a plurality of pleats, said filtering element being formed to have a substantially truncated cone shape with a hollow interior and the pleats radiating outwardly, and said truncated cone shaped filtering element having a vertical cross section of a trapezoidal shape, said filtering element having a top portion provided with an opening which is sealed by a filling material with the top portion of the filtering element being embedded in said filling material, said filling material having a lower surface facing towards the hollow interior of the filtering element, an upper surface positioned opposite said lower surface and an outer peripheral portion, said lower surface of the filling material having a central portion that protrudes into the hollow interior with the lower surface possessing an upwardly inclined shape, said upper surface of said filling material having a substantially horizontal and flat surface, said upwardly inclined lower surface of the filling material extending from the central portion to the outer peripheral portion so that the upwardly inclined lower surface intersects the pleats.

10. A filtering apparatus, comprising:
    a housing formed with an inlet through which a fluid to be treated flows into the housing and an outlet through which treated fluid drains out of the housing, said housing also being formed with a vent;
    a filtering element provided inside said housing to partition the inside of said housing into a first space that communicates with said inlet and a second space that communicates with said outlet, said filtering element being made from a porous material that has been folded to form a plurality of pleats and formed so as to have a substantially cylindrical shape with the pleats radiating outwardly, the cylindrically shaped filtering element having a bottom portion and a top portion provided with an opening;

a filling material for sealing the opening of the top portion of said filtering element with the top portion of said filtering element being embedded in said filling material, said filling material having a lower surface that is positioned at the side of said second space of said housing, at least a portion of said lower surface forming an upwardly inclined surface that intersects the pleats, with said upwardly inclined surface of said lower surface causing air bubbles generated in said second space to easily discharge to the first space.

* * * * *

UNITED STATES PATENT AND TRADEMARK OFFICE
CERTIFICATE OF CORRECTION

PATENT NO. : 5,618,425
DATED : April 8, 1997
INVENTOR(S) : Makoto MITAMURA et al It is certified that error appears in the above-indentified patent and that said Letters Patent is hereby corrected as shown below:

In column 9, line 23, delete "cortically" and insert -- conically --.
In column 9, line 45, delete "ease" and insert -- case --.

Signed and Sealed this

Eighth Day of July, 1997

Attest:

BRUCE LEHMAN

Attesting Officer    Commissioner of Patents and Trademarks